United States Patent [19]

Bergsma et al.

[11] Patent Number: 6,033,872
[45] Date of Patent: Mar. 7, 2000

[54] POLYNUCLEOTIDES ENCODING A NOVEL HUMAN 11CB SPLICE VARIANT

[75] Inventors: Derk Jon Bergsma, Berwyn, Pa.; Catherine Elizabeth Ellis, Glassboro, N.J.

[73] Assignee: SmithKline Beecham Corporation, Philadelphia, Pa.

[21] Appl. No.: 08/984,288

[22] Filed: Dec. 3, 1997

Related U.S. Application Data

[60] Provisional application No. 60/032,763, Dec. 11, 1996.

[51] Int. Cl.$^7$ ............................ C12N 15/12; C12N 15/63; C12N 15/85
[52] U.S. Cl. .................. 435/69.1; 435/325; 435/320.1; 435/252.3; 536/23.1; 536/23.5
[58] Field of Search ................................ 536/23.1, 23.5; 435/69.1, 252.3, 320.1, 325

[56] References Cited

PUBLICATIONS

Gress et al. "A Pancreatic cancer–specific expression profile", Oncogene, vol. 13, pp. 1819–1830 (1996).
GeneBank Accession #U71092.
Kolakowski, Jr., Lee F., et al. *"Characterization of a human gene related to genes encoding somatostatin receptors"*, FEBS Letters 398:253–258 (1996).
Rudinger, In "Peptide Hormones" (ed. J. A. Parsons) University Park Press, Baltimore, pp. 1–7, 1976.
Vanetti et al., GenBank Accession # X68951 and S47713 (1992).
George et al "Current Methods in Sequence Comparison and Analysis" in Macro–Molecular Sequencing and Synthesis (1988) Alan R. Liss Publications, USA pp. 127–149.

*Primary Examiner*—Anthony C. Caputa
*Assistant Examiner*—Robert C. Hayes
*Attorney, Agent, or Firm*—William T. Han; Ratner & Prestia; William T. King

[57] ABSTRACT

Human 11cb splice variant polypeptides and DNA (RNA) encoding such an 11cb splice variant and a procedure for producing such polypeptides by recombinant techniques are disclosed. Also disclosed are methods for utilizing such an 11cb splice variant for the treatment of infections, such as bacterial, fungal, protozoan and viral infections, particularly infection caused by HIV-1 or HIV-2; pain; cancers; anorexia; bulimia; asthma; Parkinson's disease; both acute and congestive heart failure; hypotension; hypertension; urinary retention; osteoporosis; angina pectoris; myocardial infarction; ulcers; allergies; benign prostatic hypertrophy and psychotic and neurological disorders, including anxiety, schizophrenia, manic depression, delirium, dementia or severe mental retardation; dyskinesias, such as Huntington's disease or Gilles dela Tourett's syndrome, among others. Antagonists against such an 11cb splice variant and their use as a therapeutic to treat infections, such as bacterial, fungal, protozoan and viral infections, particularly infection caused by HIV-1 or HIV-2; pain; cancers; anorexia; bulimia; asthma; Parkinson's disease; both acute and congestive heart failure; hypotension; hypertension; urinary retention; osteoporosis; angina pectoris; myocardial infarction; ulcers; allergies; benign prostatic hypertrophy and psychotic and neurological disorders; and dyskinesias, such as Huntington's disease or Gilles dela Tourett's syndrome, among others, are also disclosed. Also disclosed are diagnostic assays for detecting diseases related to mutations in the nucleic acid sequences and altered concentrations of the polypeptides. Also disclosed are diagnostic assays for detecting mutations in the polynucleotides encoding the 11cb splice variant and for detecting altered levels of the polypeptide in a host.

12 Claims, 2 Drawing Sheets

Nucleotide sequence of the human 11cb splice variant (SEQ ID NO: 1).

```
  1   GGTGACACTA TAGAAGGTAC GCCTGCAGGT ACCGGTCCGG AATTCCCGGG
 51   TCGACCCACG CGTCCGGGAG GGCAGTTGGG CTTGGAGGCG GCAGCGGCTG
101   CCAGGCTACG GAGGAAGACC CCCTTCCCGA CTGCGGGCT TGCGCTCCGG
151   GACAAGGTGG CAGGCGCTGG AGGCTGCCGC AGCCTGCGTG GGTGGAGGGG
201   AGCTCAGCTC GGTTGTGGGA GCAGGCGACC GGCACTGGCT GGATGGACCT
251   GGAAGCCTCG CTGCTGCCCA CTGGTCCCAA TGCCAGCAAC ACCTCTGATG
301   GCCCCGATAA CCTCACTTCG GCAGGATCAC CTCCTCGCAC GGGGAGCATC
351   TCCTACATCA ACATCATCAT GCCTTCGGTG TTCGGCACCA TCTGCCTCCT
401   GGGCATCATC GGGAACTCCA CGGTCATCTT CGCGGTCGTG AAGAAGTCCA
451   AGCTGCACTG GTGCAACAAC GTCCCCGACA TCTTCATCAT CAACCTCTCG
501   GTAGTAGATC TCCTCTTTCT CCTGGGCATG CCCTTCATGA TCCACCAGCT
551   CATGGGCAAT GGGGTGTGGC ACTTTGGGGA GACCATGTGC ACCCTCATCA
601   CGGCCATGGA TGCCAATAGT CAGTTCACCA GCACCTACAT CCTGACCGCC
651   ATGGCCATTG ACCGCTACCT GGCCACTGTC CACCCCATCT CTTCCACGAA
701   GTTCCGGAAG CCCTCTGTGG CCACCCTGGT GATCTGCCTC CTGTGGGCCC
751   TCTCCTTCAT CAGCATCACC CCTGTGTGGC TGTATGCCAG ACTCATCCCC
801   TTCCCAGGAG GTGCAGTGGG CTGCGGCATA CGCCTGCCCA ACCCAGACAC
851   TGACCTCTAC TGGTTCACCC TGTACCAGTT TTTCCTGGCC TTTGCCCTGC
901   CTTTTGTGGT CATCACAGCC GCATACGTGA GGATCCTGCA GCGCATGACG
```

FIG. 1A

```
951   TCCTCAGTGG CCCCCGCCTC CCAGCGCAGC ATCCGGCTGC GGACAAAGAG

1001  GGTGACCCGC ACAGCCATCG CCATCTGTCT GGTCTTCTTT GTGTGCTGGG

1051  CACCCTACTA TGTGCTACAG CTGACCCAGT TGTCCATCAG CCGCCCGACC

1101  CTCACCTTTG TCTACTTATA CAATGCGGCC ATCAGCTTGG GCTATGCCAA

1151  CAGCTGCCTC AACCCCTTTG TGTACATCGT GCTCTGTGAG ACGTTCCGCA

1201  AACGCTTGGT CCTGTCGGTG AAGCCTGCAG CCCAGGGGCA GCTTCGCGCT

1251  GTCAGCAACG CTCAGACGGC TGACGAGGAG AGGACAGAAA GCAAAGGCAC

1301  CTGATACTTC CCCTGCCACC CTGCACACCT CCAAGTCAGG GCACCACAAC

1351  ACGCCACCGG GAGAGATGCT CTCGTGCCGA ATTCC
```

FIG. 1B

POLYNUCLEOTIDES ENCODING A NOVEL HUMAN 11CB SPLICE VARIANT

This application claims the benefit of U.S. provisional application number 60/032,763 filed Dec. 11, 1996.

FIELD OF THE INVENTION

This invention relates, in part, to newly identified polynucleotides and polypeptides; variants and derivatives of the polynucleotides and polypeptides; processes for making the polynucleotides and the polypeptides, and their variants and derivatives; agonists and antagonists of the polypeptides; and uses of the polynucleotides, polypeptides, variants, derivatives, agonists and antagonists. In particular, in these and in other regards, the invention relates to polynucleotides and polypeptides of the human 11cb splice variant.

BACKGROUND OF THE INVENTION

This invention relates to newly identified polynucleotides, polypeptides encoded by such polynucleotides, the use of such polynucleotides and polypeptides, as well as the production of such polynucleotides and polypeptides. More particularly, the polypeptides of the present invention are human 7-transmembrane receptors. The invention also relates to inhibiting or activating the action of such polypeptides.

It is well established that many medically significant biological processes are mediated by proteins participating in signal transduction pathways that involve G-proteins and/or second messengers, e.g., cAMP (Lefkowitz, *Nature*, (1991) 351: 353–354). Herein these proteins are referred to as proteins participating in pathways with G-proteins or PPG proteins. Some examples of these proteins include the GPC receptors, such as those for adrenergic agents and dopamine (Kobilka, B. K., et al., *PNAS*, (1987), 84: 46–50; Kobilka, B. K, et al., *Science*, (1987), 238: 650–656; Bunzow, J. R., et al., *Nature*, (1988), 336:783–787), G-proteins themselves, effector proteins, e.g., phospholipase C, adenyl cyclase, and phosphodiesterase, and actuator proteins, e.g., protein kinase A and protein kinase C (Simon, M. I., et al., *Science*, 252: 802–8 (1991)).

For example, in one form of signal transduction, the effect of hormone binding is activation of the enzyme, adenylate cyclase, inside the cell. Enzyme activation by hormones is dependent on the presence of the nucleotide GTP. GTP also influences hormone binding. A G-protein connects the hormone receptor to adenylate cyclase. G-protein was shown to exchange GTP for bound GDP when activated by a hormone receptor. The GTP-carrying form then binds to activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane a-helices connected by extracellular or cytoplasmic loops. G-protein coupled receptors include a wide range of biologically active receptors, such as hormone, viral, growth factor and neuroreceptors.

G-protein coupled receptors have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include, but are not limited to, calcitonin, adrenergic, endothelin, cAMP, adenosine, muscarinic, acetylcholine, serotonin, histamine, thrombin, kinin, follicle stimulating hormone, opsins, endothelial differentiation gene-1 receptor, rhodopsins, odorant, cytomegalovirus receptors,.

Most G-protein coupled receptors have single conserved cysteine residues in each of the first two extracellular loops which form disulfide bonds that are believed to stabilize functional protein structure. The 7 transmembrane regions are designated as TM1, TM2, TM3, TM4, TM5, TM6, and TM7. TM3 has been implicated in signal transduction.

Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the b-adrenoreceptor, phosphorylation by protein kinase A and/or specific receptor kinases mediates receptor desensitization.

For some receptors, the ligand binding sites of G-protein coupled receptors are believed to comprise a hydrophilic socket formed by several G-protein coupled receptor transmembrane domains, which socket is surrounded by hydrophobic residues of the G-protein coupled receptors. The hydrophilic side of each G-protein coupled receptor transmembrane helix is postulated to face inward and form a polar ligand binding site. TM3 has been implicated in several G-protein coupled receptors as having a ligand binding site, such as the TM3 aspartate residue. TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters. See Johnson, et al., *Endoc. Rev.*, (1989)10: 317–331). Different G-protein a-subunits preferentially stimulate particular effectors to modulate various biological functions in a cell. Phosphorylation of cytoplasmic residues of G-protein coupled receptors have been identified as an important mechanism for the regulation of G-protein coupling of some G-protein coupled receptors. G-protein coupled receptors are found in numerous sites within a mammalian host.

Since, over the past 15 years, nearly 150 therapeutic agents targeting 7 transmembrane (7 TM) receptors have been successfully introduced onto the market. This indicates that these receptors have an established, proven history as therapeutic targets. Clearly, there is a need for identification and characterization of further receptors which can play a role in preventing, ameliorating or correcting dysfunctions or diseases, including, but not limited to, infections such as bacterial, fungal, protozoan and viral infections, particularly infection caused by HIV-1 or HIV-2; pain; cancers; diabetes; obesity; anorexia; bulimia; asthma; Parkinson's disease; both acute and congestive heart failure; hypotension; hypertension; urinary retention; osteoporosis; angina pectoris; myocardial infarction; ulcers; allergies; benign prostatic hypertrophy and psychotic and neurological disorders, including anxiety, schizophrenia, manic depression, delirium, dementia or severe mental retardation, and dyskinesias, such as Huntington's disease or Gilles dela Tourett's syndrome, among others.

The polypeptide of the present invention has the conserved 7 transmembrane residues, and have amino acid sequence homology to known G-protein couples receptors.

The orginal human 11cb clone has been previously disclosed by Applicants in PCT WO 96/18651, published Jun. 20, 1996.

SUMMARY OF THE INVENTION

Toward these ends, and others, it is an object of the present invention to provide polypeptides, inter alia, that have been identified as a novel human 11cb splice variant by homology between the amino acid sequence set out in FIG. 1 (SEQ ID NO: 2) and known amino acid sequences of other proteins such as mouse cDNA, rat calcitonin receptor A, rat calcitonin receptor B, and hormone receptor EMR1.

It is a further object of the invention, moreover, to provide polynucleotides that encode this 11cb splice variant, particularly polynucleotides that encode the polypeptide herein designated 11cb splice variant.

In a particularly preferred embodiment of this aspect of the invention the polynucleotide comprises the region encoding the 11cb splice variant in the sequence set out in FIG. 1 (SEQ ID NO: 1).

In accordance with this aspect of the invention there are provided isolated nucleic acid molecules encoding this 11cb splice variant, including mRNAs, cDNAs, genomic DNAs and, in further embodiments of this aspect of the invention, biologically, diagnostically, clinically or therapeutically useful variants, analogs or derivatives thereof, or fragments thereof, including fragments of the variants, analogs and derivatives.

Among the particularly preferred embodiments of this aspect of the invention are naturally occurring allelic variants of human 11cb splice variant.

It also is an object of the invention to provide 11cb splice variant polypeptides, particularly 11cb splice variant polypeptides, that may be employed for therapeutic purposes, for example, to treat infections, such as bacterial, fungal, protozoan and viral infections, particularly infection caused by HIV-1 or HIV-2; pain; cancers; diabetes; obesity; anorexia; bulimia; asthma; Parkinson's disease; both acute and congestive heart failure; hypotension; hypertension; urinary retention; osteoporosis; angina pectoris; myocardial infarction; ulcers; allergies; benign prostatic hypertrophy and psychotic and neurological disorders, including anxiety, schizophrenia, manic depression, delirium, dementia or severe mental retardation, and dyskinesias, such as Huntington's disease or Gilles dela Tourett's syndrome, among others.

In accordance with this aspect of the invention there are provided novel polypeptides referred to herein as 11cb splice variant as well as biologically, diagnostically or therapeutically useful fragments, variants and derivatives thereof, variants and derivatives of the fragments, and analogs of the foregoing.

Among the particularly preferred embodiments of this aspect of the invention are variants of 11cb splice variant encoded by naturally occurring alleles of the 11cb splice variant gene.

In accordance with another aspect of the present invention there are provided methods of screening for compounds which bind to and activate or inhibit activation of the receptor polypeptides of the present invention and for receptor ligands.

It is another object of the invention to provide a process for producing the aforementioned polypeptides, polypeptide fragments, variants and derivatives, fragments of the variants and derivatives, and analogs of the foregoing. In a preferred embodiment of this aspect of the invention there are provided methods for producing the aforementioned 11cb splice variant polypeptides comprising culturing host cells having expressibly incorporated therein an exogenously-derived 11cb splice variant-encoding polynucleotide under conditions for expression of 11cb splice variant in the host and then recovering the expressed polypeptide.

In accordance with another object the invention there are provided products, compositions, processes and methods that utilize the aforementioned polypeptides and polynucleotides for research, biological, clinical and therapeutic purposes, inter alia.

In accordance with certain preferred embodiments of this aspect of the invention, there are provided products, compositions and methods, inter alia, for, among other things: assessing 11cb splice variant expression in cells by determining 11cb splice variant polypeptides or 11cb splice variant-encoding mRNA; to treat infections, such as bacterial, fungal, protozoan and viral infections, particularly infection caused by HIV-1 or HIV-2; pain; cancers; diabetes; obesity; anorexia; bulimia; asthma; Parkinson's disease; both acute and congestive heart failure; hypotension; hypertension; urinary retention; osteoporosis; angina pectoris; myocardial infarction; ulcers; allergies; benign prostatic hypertrophy and psychotic and neurological disorders, including anxiety, schizophrenia, manic depression, delirium, dementia or severe mental retardation, and dyskinesias, such as Huntington's disease or Gilles dela Tourett's syndrome; among others, in vitro, ex vivo or in vivo by exposing cells to 11cb splice variant polypeptides or polynucleotides as disclosed herein; assaying genetic variation and aberrations, such as defects, in 11cb splice variant genes; and administering an 11cb splice variant polypeptide or polynucleotide to an organism to augment 11cb splice variant function or remediate 11cb splice variant dysfunction.

In accordance with still another embodiment of the present invention, there is provided a process of using such activating compounds to stimulate the receptor polypeptide of the present invention for the treatment of conditions related to the under-expression of 11cb splice variant.

In accordance with another aspect of the present invention there is provided a process of using such inhibiting compounds for treating conditions associated with over-expression of the 11cb splice variant.

In accordance with yet another aspect of the present invention there is provided non-naturally occurring synthetic, isolated and/or recombinant 11cb splice variant polypeptides which are fragments, consensus fragments and/or sequences having conservative amino acid substitutions, of at least one domain of the 11cb splice variant of the present invention, such that the receptor may bind 11cb splice variant ligands, or which may also modulate, quantitatively or qualitatively, 11cb splice variant ligand binding.

In accordance with still another aspect of the present invention there are provided synthetic or recombinant 11cb splice variant polypeptides, conservative substitution and derivatives thereof, antibodies thereto, anti-idiotype antibodies, compositions and methods that can be useful as potential modulators 11cb splice variant function, by binding to ligands or modulating ligand binding, due to their expected biological properties, which may be used in diagnostic, therapeutic and/or research applications.

It is still another object of the present invention to provide synthetic, isolated or recombinant polypeptides which are designed to inhibit or mimic various 11cb splice variants or fragments thereof, as receptor types and subtypes.

In accordance with certain preferred embodiments of this and other aspects of the invention there are provided probes that hybridize to human 11cb splice variant sequences.

In certain additional preferred embodiments of this aspect of the invention there are provided antibodies against 11cb splice variant polypeptides. In certain particularly preferred embodiments in this regard, the antibodies are highly selective for human 11cb splice variant.

In accordance with another aspect of the present invention, there are provided 11cb splice variant agonists. Among preferred agonists are molecules that mimic the 11cb splice variant, that bind to 11cb splice variant-binding molecules or receptor molecules, and that elicit or augment 11cb splice variant-induced responses. Also among preferred agonists are molecules that interact with 11cb splice variant or 11cb splice variant polypeptides, or with other modulators of 11cb splice variant activities, and thereby potentiate or augment an effect of 11cb splice variant or more than one effect of 11cb splice variant.

In accordance with yet another aspect of the present invention, there are provided 11cb splice variant antagonists. Among preferred antagonists are those which mimic the 11cb splice variant so as to bind to the 11cb splice variant receptor or binding molecules but not elicit an 11cb splice variant-induced response or more than one 11cb splice variant-induced response. Also among preferred antagonists are molecules that bind to or interact with the 11cb splice variant so as to inhibit an effect of 11cb splice variant or more than one effect of 11cb splice variant or which prevent expression of 11cb splice variant.

In a further aspect of the invention there are provided compositions comprising an 11cb splice variant polynucleotide or an 11cb splice variant polypeptide for administration to cells in vitro, to cells ex vivo and to cells in vivo, or to a multicellular organism. In certain particularly preferred embodiments of this aspect of the invention, the compositions comprise an 11cb splice variant polynucleotide for expression of an 11cb splice variant polypeptide in a host organism for treatment of disease. Particularly preferred in this regard is expression in a human patient for treatment of a dysfunction associated with aberrant endogenous activity of the 11cb splice variant.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIG. 1 (SEQ ID NO:1) and SEQ ID NO:2 show, respectively the nucleotide and deduced amino acid sequence of the human 11cb splice variant.

GLOSSARY

The following illustrative explanations are provided to facilitate understanding of certain terms used frequently herein. The explanations are provided as a convenience and are not meant to limit the invention.

"Genetic element" generally means a polynucleotide comprising a region that encodes a polypeptide or a region that regulates replication, transcription or translation or other processes important to expression of the polypeptide in a host cell, or a polynucleotide comprising both a region that encodes a polypeptide and a region operably linked thereto that regulates expression.

Genetic elements may be comprised within a vector that replicates as an episomal element; that is, as a molecule physically independent of the host cell genome. They may be comprised within mini-chromosomes, such as those that arise during amplification of transfected DNA by methotrexate selection in eukaryotic cells. Genetic elements also may be comprised within a host cell genome, not in their natural state but, rather, following manipulation such as isolation, cloning and introduction into a host cell in the form of purified DNA or in a vector, among others.

"Isolated" means altered "by the hand of man" from its natural state; i.e., that, if it occurs in nature, it has been changed or removed from its original environment, or both. For example, a naturally occurring polynucleotide or a polypeptide naturally present in a living animal in its natural state is not "isolated," but the same polynucleotide or polypeptide separated from the coexisting materials of its natural state is "isolated", as the term is employed herein.

"Polynucleotide(s)" generally refers to any polyribonucleotide or polydeoxribonucleotide, which may be unmodified RNA or DNA or modified RNA or DNA. Polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. The term polynucleotide also includes DNAs or RNAs containing one or more modified bases. Thus, DNAs or RNAs with backbones modified for stability or for other reasons are polynucleotides as that term is intended herein. Moreover, DNAs or RNAs comprising unusual bases, such as inosine, or modified bases, such as tritylated bases, to name just two examples, are polynucleotides. It will be appreciated that a great variety of modifications have been made to DNA and RNA that serve many useful purposes known to those of skill in the art. The term polynucleotide, as it is employed herein, embraces such chemically, enzymatically or metabolically modified forms of polynucleotides, as well as the chemical forms of DNA and RNA characteristic of viruses and cells, including inter alia simple and complex cells. The term polynucleotide, as used herein, also embraces relatively short polynucleotides, often referred to as oligonucleotides.

"Polypeptides", as used herein, includes all polypeptides as described below. The basic structure of polypeptides is well known and has been described in the art. The term is used herein to refer to any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. Polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, or by chemical modification techniques which are well known to the art. Even the common modifications that occur naturally in polypeptides are too numerous to list exhaustively here, but they are well described in basic texts and in more detailed monographs, as well as in a voluminous research literature, and thus are well known to those of skill in the art. Among the known modifications which may be present in polypeptides of the present invention are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and are described in most basic texts, such as, for instance, PROTEINS—STRUCTURE AND MOLECULAR PROPERTIES, 2d Ed., T. E. Creighton, W. H. Freeman and Company, New York, 1993. Many detailed reviews are available on this subject, such as, for example, those provided by Wold, F., POSTTRANSLATIONAL PROTEIN MODIFICATIONS: PERSPECTIVES AND PROSPECTS, pgs. 1–12 in POSTTRANSLATIONAL COVALENT MODIFICATION OF PROTEINS, B. C. Johnson, Ed., Academic Press, New York, 1983; Seifter, et al., "Analysis for protein modifications and nonprotein cofactors", *Meth. Enzymol.*, 1990, 182: 626–646 and Rattan, et al., "Protein Synthesis: Posttranslational Modifications and Aging", *Ann. N.Y Acad. Sci.*, 1992, 663: 48–62.

Polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli*, prior to processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell's posttranslational modification capacity and the modification signals present in the polypeptide amino acid sequence. For instance, as is well known, glycosylation often does not occur in bacterial hosts such as *E. coli*. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to express efficiently mammalian proteins having the native patterns of glycosylation, inter alia. Similar considerations apply to other modifications.

It will be appreciated that the same type of modification may be present in the same or varying degrees at several sites in a given polypeptide. Also, a given polypeptide may contain many types of modifications.

The term polypeptide encompasses all such modifications, particularly those that are present in polypeptides synthesized by expressing a polynucleotide in a host cell.

"Variant(s)," as the term is used herein, are polynucleotides or polypeptides that differ from a reference polynucleotide or polypeptide respectively. Variants in this sense are described below and elsewhere in the present disclosure in greater detail. (1) A polynucleotide that differs in nucleotide sequence from another, reference polynucleotide. Changes in the nucleotide sequence of the variant may be silent, i.e., they may not alter the amino acids encoded by the polynucleotide. Where alterations are limited to silent changes of this type a variant will encode a polypeptide with the same amino acid sequence as the reference polypeptide. Changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below. (2) A polypeptide that differs in amino acid sequence from another, reference polypeptide. Generally, differences are limited so that the sequences of the reference and the variant are closely similar overall and, in many region, identical. A variant and reference polypeptide may differ in amino acid sequence by one or more substitutions, additions, deletions, fusions and truncations, which may be present in any combination. (3) A variant may also be a fragment of a polynucleotide or polypeptide of the invention that differs from a reference polynucleotide or polypeptide sequence by being shorter than the reference sequence, such as by a terminal or internal deletion. A variant of a polypeptide of the invention also includes a polypeptide which retains essentially the same biological function or activity as such polypeptide, e.g., proproteins which can be activated by cleavage of the proprotein portion to produce an active mature polypeptide. (4) A variant may also be (i) one in which one or more of the amino acid residues are substituted with a conserved or non-conserved amino acid residue (preferably a conserved amino acid residue) and such substituted amino acid residue may or may not be encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. (5) A variant of the polynucleotide or polypeptide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms, or may be made by recombinant means. Among polynucleotide variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions. All such variants defined above are deemed to be within the scope of those skilled in the art from the teachings herein and from the art.

"Binding molecules" (or otherwise called "interaction molecules" or "receptor component factors") refer to molecules, including ligands, that specifically bind to or interact with receptor polypeptides of the present invention. Such binding molecules are a part of the present invention. Binding molecules may also be non-naturally occurring, such as antibodies and antibody-derived reagents that bind specifically to polypeptides of the invention.

"Identity" or "similarity" as known in the art, are relationships between two or more polypeptide sequences or two or more polynucleotide sequences, as determined by comparing the sequences. "Similarity" between two polypeptides is determined by comparing the amino acid sequence and its conserved amino acid substitutes of one polypeptide to the sequence of a second polypeptide. "Identity" which means the degree of sequence relatedness between polypeptide or polynucleotide sequences, as the case may be, as determined by the match between strings of such sequences. The term, "homology," as it is used herein, embraces both identity and similarity. Both identity and similarity can be readily calculated (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity and similarity between two polynucleotide or polypeptide sequences, the terms "identity" and "similarity" are well known to skilled artisans (Carillo, H., and Lipton, D., *SIAM J. Applied Math.,* 1988, 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., SIAM *J. Applied Math.,* 1988, 48: 1073. Preferred methods to determine identity are designed to give the largest match between the two sequences tested. Methods to determine identity and similarity are codified in computer programs. Preferred computer program methods to determine identity and similarity between two sequences include, but are not limited to, GCS program package (Devereux, J., et al., *Nucleic Acids Research,* 1984, 12(1):387), BLASTP, BLASTN, FASTA (Atschul, S. F., et al., *J. Molec. Biol.,* 1990, 215: 403).

DESCRIPTION OF THE INVENTION

The invention relates, inter alia, to polypeptides and polynucleotides of a novel 11cb splice variant, which is related by amino acid sequence homology to the 11cb splice variant encoded by mouse cDNA. The invention relates especially to the 11cb splice variant having the nucleotide and amino acid sequences set out in SEQ ID NOS: 1 and 2.

Polynucleotides

In accordance with one aspect of the present invention, there are provided isolated polynucleotides which encode the 11cb splice variant polypeptide having the deduced amino acid sequence of SEQ ID NO: 2.

The 11cb splice variant of the invention is structurally related to other proteins of the 7-transmembrane receptor family, as shown by the results of sequencing the cDNA. The cDNA sequence contains an open reading frame encoding a protein of 353 amino acids. The nucleotide sequence of the 11cb splice variant of SEQ ID NO: 1 has about 90% identity over its entirety with the original human 11cb clone of WO 96/18651, published Jun. 20, 1996.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

The coding sequence which encodes the polypeptide may be identical over its entire length to the coding sequence of the polynucleotide shown in SEQ ID NO: 1. It also may be a polynucleotide with a different sequence, which, as a result of the redundancy (degeneracy) of the genetic code, also encodes the polypeptide of SEQ ID NO: 2.

Polynucleotides of the present invention which encode the polypeptide of SEQ ID NO: 2 may include, but are not limited to, the coding sequence for the mature polypeptide, by itself, the coding sequence for the mature polypeptide and additional coding sequences, such as those encoding a leader or secretory sequence, such as a pre-, or pro- or preproprotein sequence; and the coding sequence of the mature polypeptide, with or without the aforementioned additional coding sequences, together with additional, non-coding sequences, including, but not limited to, introns and non-coding 5' and 3' sequences, such as the transcribed, non-translated sequences that play a role in transcription, and mRNA processing, including splicing and polyadenylation signals, for example, for ribosome binding and stability of mRNA. Coding sequences which provide additional functionalities may also be incorporated into the polypeptide. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in the pQE vector (Qiagen, Inc.). As described in Gentz, et al., *Proc. Natl. Acad. Sci., USA,* 1989, 86: 821–824, for instance, hexa-histidine provides for convenient purification of the fusion protein. In other embodiment the marker sequence is a HA tag. Many other such tags are commercially abatable.

In accordance with foregoing, the term "polynucleotide encoding a polypeptide" also encompasses polynucleotides that include a single continuous region or discontinuous regions encoding the polypeptide (for example, interrupted by introns) together with additional regions, that also may contain coding and/or non-coding sequences.

The present invention further relates to variants of the polynucleotides which encode for variants of the polypeptide having the deduced amino acid sequence of SEQ ID NO: 2.

Among particularly preferred embodiments of the invention are polynucleotides encoding polypeptides having the amino acid sequence of the 11cb splice variant set out in SEQ ID NO: 2 and variants thereof.

Further preferred embodiments are polynucleotides encoding variants of the 11cb splice variant that have the amino acid sequence of the 11cb splice variant polypeptide of SEQ ID NO: 1 in which several, 5 to 10, 1 to 5, 1 to 3, 2, 1 or no amino acid residues are substituted, deleted or added, in any combination Further preferred embodiments of the invention are polynucleotides that are at least 91% identical over their entire length to a polynucleotide encoding the 11cb splice variant polypeptide having the amino acid sequence set out in SEQ ID NO: 2, and polynucleotides which are complementary to such polynucleotides. In this regard, polynucleotides at least 95% identical over their entire length to the same are particularly preferred, with those at least 97–99% being the most preferred.

Particularly preferred embodiments are polynucleotides which encode polypeptides, which retain substantially the same biological function or activity as the mature polypeptide encoded by the cDNA of SEQ ID NO: 1.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

Polynucleotides of the invention as discussed above, may be used as hybridization probes for cDNA and genomic DNA, to isolate full-length cDNAs and genomic clones encoding the 11cb splice variant and to isolate cDNA and genomic clones of other genes that have a high sequence similarity to the 11cb splice variant gene. Such hybridization techniques are known to those of skill in the art. The probes generally will comprise at least 15 nucleotides. Preferably, such probes will have at least 30 nucleotides and may have at least 50 nucleotides. Particularly preferred probes will range between 30 and 50 nucleotides.

The polynucleotides and polypeptides of the present invention may be employed as research reagents and materials for discovery of treatments and diagnostics to human disease, as further discussed herein relating to polynucleotide assays.

A polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Polypeptides

The present invention further relates to a human 11cb splice variant polypeptide which has the deduced amino acid sequence of SEQ ID NO: 2.

The polypeptide of the present invention may be a recombinant polypeptide, a natural polypeptide or a synthetic polypeptide. In certain preferred embodiments, it is a recombinant polypeptide.

Among the particularly preferred embodiments of the invention are polypeptides having the amino acid sequence of 11cb splice variant, set out in SEQ ID NO: 2, and variants thereof Other preferred embodiments of the invention are polypeptides having the amino acid sequence of 11cb splice variant, and variants thereof Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr.

Further preferred are variants of the fragments, having the amino acid sequence of the 11cb splice variant polypeptide of SEQ ID NO: 2, in which several, 5 to 10, 1 to 5, 1 to 3, 2, 1 or no amino acid residues are substituted, deleted or added, in any combination.

Especially preferred among these are silent substitutions, additions and deletions, which do not alter the properties and activities of the 11cb splice variant. Also especially preferred in this regard are conservative substitutions.

Most highly preferred are polypeptides having the amino acid sequence of SEQ ID NO: 2 without substitutions.

The polypeptides and polynucleotides of the present invention are preferably provided in an isolated form, and preferably are purified to homogeneity.

The polypeptides of the present invention include the polypeptide of SEQ ID NO: 2 (in particular the mature polypeptide) as well as polypeptides which have at least 91% identity to the polypeptide of SEQ ID NO: 2.

Fragments

Also among preferred embodiments of this aspect of the present invention are polypeptides comprising variants that are fragments of the 11cb splice variant, most particularly fragments of the 11cb splice variant having the amino acid set out in SEQ ID NO:2, and variants of the 11cb splice variant of SEQ ID NO:2.

In this regard, a fragment is a polypeptide having an amino acid sequence that entirely is the same as part but not all of the amino acid sequence of the aforementioned 11cb splice variant polypeptides and variants thereof.

Such fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of an 11cb splice variant polypeptide of the present comprised within a precursor polypeptide designed for expression in a host and having heterologous pre and pro-polypeptide regions fused to the amino terminus of the 11cb splice variant fragment and an additional region fused to the carboxyl terminus of the fragment. Therefore, fragments in one aspect of the meaning intended herein, refers to the portion or portions of a fusion polypeptide or fusion protein derived from the 11cb splice variant.

In this context, "about" herein includes the particularly recited ranges larger or smaller by several, 5, 4, 3, 2 or 1 amino acid at either extreme or at both extremes.

Preferred fragments of the invention include, for example, truncation polypeptides of the 11cb splice variant. Truncation polypeptides include 11cb splice variant polypeptides having the amino acid sequence of SEQ ID NO: 2, or of variants thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Fragments having the size ranges set out about also are preferred embodiments of truncation fragments, which are especially preferred among fragments generally Also preferred in this aspect of the invention are fragments characterized by structural or functional attributes of the 11cb splice variant. Preferred embodiments of the invention in this regard include fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions of the 11cb splice variant, and combinations of such fragments.

Preferred regions are those that mediate activities of the 11cb splice variant. Most highly preferred in this regard are fragments that have a chemical, biological or other activity of the 11cb splice variant, including those with a similar activity or an improved activity, or with a decreased undesirable activity. Further preferred polypeptide fragments are those that are antigenic or immunogenic in an animal, especially in a human.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspond to the preferred fragments, as discussed above.

Vectors, Host Cells, Expression

The present invention also relates to vectors which comprise a polynucleotide or polynucleotides of the present invention, and host cells which are genetically engineered with vectors of the invention and the production of polypeptides of the invention by recombinant techniques.

Host cells can be genetically engineered to incorporate polynucleotides and express polypeptides of the present invention. Introduction of a polynucleotides into the host cell can be affected by calcium phosphate transfection, DEAE-dextran mediated transfection, transvection, microinjection, cationic lipid-mediated transfection, electroporation, transduction, scrape loading, ballistic introduction, infection or other methods. Such methods are described in many standard laboratory manuals, such as Davis, et al., BASIC METHODS IN MOLECULAR BIOLOGY, (1986) and Sambrook, et al., MOLECULAR CLONING: A LABORATORY MANUAL, 2nd Ed., Cold Spring Harbor Laboratory Press, Cold Spring Harbor, N.Y. (1989).

Representative examples of appropriate hosts include bacterial cells, such as streptococci, staphylococci, *E. coli*, streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

Polynucelotide constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., MOLECULAR CLONING: A LABORATORY MANUAL, 2nd Ed., Cold Spring Harbor Laboratory Press, Cold Spring Harbor, N.Y. (1989).

In accordance with this aspect of the invention the vector may be, for example, a plasmid vector, a single or double-stranded phage vector, a single or double-stranded RNA or DNA viral vector. Plasmids generally are designated herein by a lower case p preceded and/or followed by capital letters and/or numbers, in accordance with standard naming conventions that are familiar to those of skill in the art. Starting plasmids disclosed herein are either commercially available, publicly available, or can be constructed from available plasmids by routine application of well known, published procedures. Many plasmids and other cloning and expression vectors that can be used in accordance with the present invention are well known and readily available to those of skill in the art.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

A great variety of expression vectors can be used to express a polypeptide of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques, such as, for example, those set forth in Sambrook, et al., MOLECULAR CLONING, A LABORATORY MANUAL, 2nd Ed.; Cold Spring Harbor Laboratory Press, Cold Spring Harbor, N.Y. (1989).

The DNA sequence in the expression vector is operatively linked to appropriate expression control sequence(s), including, for instance, a promoter to direct mRNA transcription. Representatives of such promoters include, but are not limited to, the phage lambda PL promoter, the E. coli lac, trp and tac promoters, the SV40 early and late promoters and promoters of retroviral LTRs.

In general, expression constructs will contain sites for transcription initiation and termination, and, in the transcribed region, a ribosome binding site for translation. The coding portion of the mature transcripts expressed by the constructs will include a translation initiating codon, for example, AUG or GUG, at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as transcription factors, repressor binding sites and termination, among others.

Vectors for propagation and expression generally will include selectable markers and amplification regions, such as, for example, those set forth in Sambrook et al.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia, and pBR322 (ATCC 37017). Among preferred eukaryotic vectors are pWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("CAT") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available, such as pKK232-8 and pCM7. Promoters for expression of polynucleotides of the present invention include not only well known and readily available promoters, but also promoters that readily may be obtained by the foregoing technique, using a reporter gene.

Among known prokaryotic promoters suitable for expression of polynucleotides and polypeptides in accordance with the present invention are the E. coli lacI and lacZ and promoters, the T3 and T7 promoters, the gpt promoter, the lambda PR, PL promoters and the trp promoter.

Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

Recombinant expression vectors will include, for example, origins of replication, a promoter preferably derived from a highly-expressed gene to direct transcription of a downstream structural sequence, and a selectable marker to permit isolation of vector containing cells after exposure to the vector.

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the codon that initiates translation of the polypeptide to be expressed, for example AUG or GUG. Generally, there will be no other open reading frames that begin with an initiation codon, usually AUG, and lie between the ribosome binding site and the initiation codon. Also, generally, there will be a translation stop codon at the end of the polypeptide and there will be a polyadenylation signal in constructs for use in eukaryotic hosts. Transcription termination signal appropriately disposed at the 3' end of the transcribed region may also be included in the polynucleotide construct.

For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N- or C-terminus of the polypeptide to improve stability and persistence in the host cell, during purification or during subsequent handling and storage. Also, region also may be added to the polypeptide to facilitate purification. Such regions may be removed prior to final preparation of the polypeptide. The addition of peptide moieties to polypeptides to engender secretion or excretion, to improve stability or to facilitate purification, among others, are familiar and routine techniques in the art. A preferred fusion protein comprises a heterologous region from immunolglobulin that is useful to solubilize or purify polypeptides. For example, EP-A-O 464 533 (Canadian counterpart 2045869) discloses fusion proteins comprising various portions of constant region of immunoglobin molecules together with another protein or part thereof. In drug discovery, for example, proteins have been fused with antibody Fc portions for the purpose of high-throughput screening assays to identify antagonists. See, D. Bennett, et al., *Journal of Molecular Recognition,* 8: 52–58 (1995) and K. Johanson, et al., *The Journal of Biological Chemistry,* 270 (16): 9459–9471 (1995).

Mammalian expression vectors may comprise an origin of replication, a suitable promoter and enhancer, and also any necessary ribosome binding sites, polyadenylation regions, splice donor and acceptor sites, transcriptional termination sequences, and 5' flanking non-transcribed sequences that are necessary for expression.

Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

The 11cb splice variant polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding protein may be employed to regenerate active conformation when the polypeptide is denatured during isolation and or purification.

Polynucleotide Assays

This invention also relates to the use of 11cb splice variant polynucleotides to detect complementary polynucleotides for use, for example, as a diagnostic reagent. Detection of a mutated form of the 11cb splice variant associated with a dysfunction will provide a diagnostic tool that can add to or define diagnosis of a disease or susceptibility to a disease which results from under-expression, over-expression or altered expression of the 11cb splice variant. Individuals carrying mutations in the human 11cb splice variant gene may be detected at the DNA level by a variety of techniques. Nucleic acids for diagnosis may be obtained from a patient's cells, such as from blood, urine, saliva, tissue biopsy or autopsy material. The genomic DNA may be used directly for detection or may be amplified enzymatically by using PCR prior to analysis. PCR (Saiki, et al, *Nature*, 1986, 324:163–166). RNA or cDNA may also be used in similar fashion. As an example, PCR primers complementary to the nucleic acid encoding the 11cb splice variant can be used to identify and analyze 11cb splice variant expression and mutations. For example, deletions and insertions can be detected by a change in size of the amplified product in comparison to the normal genotype. Point mutations can be identified by hybridizing amplified DNA to radiolabeled 11cb splice variant RNA or, radiolabeled 11cb splice variant antisense DNA sequences. Perfectly matched sequences can be distinguished from mismatched duplexes by RNase A digestion or by differences in melting temperatures.

Sequence differences between a reference gene and genes having mutations may also be revealed by direct DNA sequencing. In addition, cloned DNA segments may be employed as probes to detect specific DNA segments. The sensitivity of such methods can be greatly enhanced by appropriate use of PCR or other amplification methods. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alterations in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures. See, e.g., Myers, et al., *Science,* 1985, 230: 1242).

Sequence changes at specific locations may also be revealed by nuclease protection assays, such as RNase and S1 protection or the chemical cleavage method (e.g., Cotton, et al., *Proc. Natl. Acad. Sci., USA,* 1985, 85: 4397–4401).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA. In addition to more conventional gel-electrophoresis and DNA sequencing, mutations can also be detected by in situ analysis.

In accordance with a further aspect of the invention, there is provided a process for diagnosing or determining a susceptibility to infections such as bacterial, fungal, protozoan and viral infections, particularly infection caused by HIV-1 or HIV-2; pain; cancers; diabetes; obesity; anorexia; bulimia; asthma; Parkinson's disease; both acute and congestive heart failure; hypotension; hypertension; urinary retention; osteoporosis; angina pectoris; myocardial infarction; ulcers; allergies; benign prostatic hypertrophy and psychotic and neurological disorders, including anxiety, schizophrenia, manic depression, delirium, dementia or severe mental retardation, and dyskinesias, such as Huntington's disease or Gilles dela Tourett's syndrome, among others, through detection of mutation in the 11cb splice variant gene by the methods described; and the nucleic acid sequences described above may be employed for such methods.

The invention provides a process for diagnosing diseases, infections such as bacterial, fungal, protozoan and viral infections, particularly infection caused by HIV-1 or HIV-2; pain; cancers; diabetes; obesity; anorexia; bulimia; asthma; Parkinson's disease; both acute and congestive heart failure; hypotension; hypertension; urinary retention; osteoporosis; angina pectoris; myocardial infarction; ulcers; allergies; benign prostatic hypertrophy and psychotic and neurological disorders, including anxiety, schizophrenia, manic depression, delirium, dementia or severe mental retardation, and dyskinesias, such as Huntington's disease or Gilles dela Tourett's syndrome, among others; comprising determining from a sample derived from a patient an abnormally decreased or increased level of expression of polynucleotide having the sequence of FIG. 1 (SEQ ID NO: 1). Decreased or increased expression of polynucleotide can be measured using any of the methods well known in the art for the quantitation of polynucleotides, such as, for example, PCR, RT-PCR, RNase protection, Northern blotting and other hybridization methods.

Chromosome Assays

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

It is then necessary to determine the differences in the cDNA or genomic sequence between affected and unaffected individuals. If a mutation is observed in some or all of the affected individuals but not in any normal individuals, then the mutation is likely to be the causative agent of the disease.

Polypeptide Assays

The present invention also relates to a diagnostic assays such as quantitative and diagnostic assays for detecting levels of the 11cb splice variant protein in cells and tissues, including determination of normal and abnormal levels. Thus, for instance, a diagnostic assay in accordance with the invention for detecting over-expression of the 11cb splice variant protein compared to normal control tissue samples may be used to detect the presence of a disease/disorder such as infections, including bacterial, fungal, protozoan and viral infections, particularly infection caused by HIV-1 or HIV-2; pain; cancers; diabetes; obesity; anorexia; bulimia; asthma; Parkinson's disease; both acute and congestive heart failure; hypotension; hypertension; urinary retention; osteoporosis; angina pectoris; myocardial infarction; ulcers; allergies; benign prostatic hypertrophy and psychotic and neurological disorders, including anxiety, schizophrenia, manic depression, delirium, dementia or severe mental retardation; and dyskinesias, such as Huntington's disease or Gilles dela Tourett's syndrome, among others. Assay techniques that can be used to determine levels of a protein, such as an 11cb splice variant protein of the present invention, in a sample derived from a host are well-known to those of skill in the art. Such assay methods include radioimmunoassays, competitive-binding assays, Western Blot analysis and ELISA assays. Among these ELISAs are frequently preferred. An ELISA assay initially comprises preparing an antibody specific to the 11cb splice variant, preferably a monoclonal antibody. In addition, a reporter antibody generally is prepared which binds to the monoclonal antibody. The reporter antibody is attached a detectable reagent such as a radioactive, fluorescent or enzymatic reagent, in this example horseradish peroxidase enzyme.

To carry out an ELISA a sample is removed from a host and incubated on a solid support, e.g., a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any 11cb splice variant proteins attached to the polystyrene dish. Unbound monoclonal antibody is washed out with buffer. The reporter antibody linked to horseradish peroxidase is placed in the dish resulting in binding of the reporter antibody to any monoclonal antibody bound to the 11cb splice variant. Unattached reporter antibody is then washed out. Reagents for peroxidase activity, including a colorimetric substrate, are then added to the dish. Immobilized peroxidase, linked to the 11cb splice variant through the primary and secondary antibodies, produces a colored reaction product. The amount of color developed in a given time period indicates the amount of the 11cb splice variant protein present in the sample. Quantitative results typically are obtained by reference to a standard curve.

A competition assay may be employed wherein antibodies specific to the 11cb splice variant attached to a solid support and labeled 11cb splice variant and a sample derived from the host are passed over the solid support. The amount of detected label attached to the solid support can be correlated to a quantity of 11cb splice variant in the sample.

Antibodies

The polypeptides, their fragments or other derivatives, or analogs thereof, or cells expressing them can also be used as immunogens to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptide itself. In this manner, even a sequence encoding only a fragment of the polypeptide can be used to generate antibodies binding the whole native polypeptide. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler, et al, *Nature*, (1975), 256: 495–497, the trioma technique, the human B-cell hybridoma technique (Kozbor, et al., *Immunology Today*, (1983), 4: 72 and the EBV-hybridoma technique to produce human monoclonal antibodies (Cole, et al, pg. 77–96 in MONOCLONAL ANTIBODIES AND CANCER THERAPY, Alan R. Liss, Inc. (1985).

Techniques described for the production of single chain antibodies (U.S. Pat. No. 4,946,778) can be adapted to produce single chain antibodies to immunogenic polypeptide products of this invention. Also, transgenic mice, or other organisms including other mammals, may be used to express humanized antibodies to immunogenic polypeptide products of this invention.

The above-described antibodies may be employed to isolate or to identify clones expressing the polypeptide or purify the polypeptide of the present invention by attachment of the antibody to a solid support for isolation and/or purification by affinity chromatography.

Antibodies against the 11cb splice variant may also be employed to inhibit infections, such as bacterial, fungal, protozoan and viral infections, particularly infection caused by HIV-1 or HIV-2; pain; cancers; diabetes; obesity; anorexia; bulimia; asthma; Parkinson's disease; both acute and congestive heart failure; hypotension; hypertension; urinary retention; osteoporosis; angina pectoris; myocardial infarction; ulcers; allergies; benign prostatic hypertrophy and psychotic and neurological disorders, including anxiety, schizophrenia, manic depression, delirium, dementia or severe mental retardation, and dyskinesias, such as Huntington's disease or Gilles dela Tourett's syndrome, among others.

11cb Splice Variant Binding Molecules and Assays

The 11cb splice variant can be used to isolate proteins which interact with it; this interaction can be a target for interference. Inhibitors of protein-protein interactions between the 11cb splice variant and other factors could lead to the development of pharmaceutical agents for the modulation of 11cb splice variant activity.

Thus, this invention also provides a method for identification of binding molecules to the 11cb splice variant. Genes encoding proteins for binding molecules to the 11cb splice variant can be identified by numerous methods known to those of skill in the art, for example, ligand panning and FACS sorting. Such methods are described in many laboratory manuals such as, for instance, Coligan, et al., *Current Protocols in Immunology* 1: Chapter 5 (1991) and Rivett, A. J., *Biochem.* (1993), 291: 1–10.

For example, the yeast two-hybrid system provides methods for detecting the interaction between a first test protein and a second test protein, in vivo, using reconstitution of the activity of a transcriptional activator. The method is disclosed in U.S. Pat. No. 5,283,173; reagents are available from Clontech and Stratagene. Briefly, 11cb splice variant cDNA is fused to a Gal4 transcription factor DNA binding domain and expressed in yeast cells. cDNA library members obtained from cells of interest are fused to a transactivation domain of Gal4. cDNA clones which express proteins which can interact with the 11cb splice variant will lead to reconstitution of Gal4 activity and transactivation of expression of a reporter gene such as Gal1-lacZ.

An alternative method is screening of λgt11, λLZAP (Stratagene) or equivalent cDNA expression libraries with recombinant 11cb splice variant. Recombinant 11cb splice variant protein or fragments thereof are fused to small peptide tags such as FLAG, HSV or GST. The peptide tags can possess convenient phosphorylation sites for a kinase such as heart muscle creatine kinase or they can be biotinylated. Recombinant 11cb splice variant can be phosphorylated with 32[P] or used unlabeled and detected with streptavidin or antibodies against the tags. λgt11cDNA expression libraries are made from cells of interest and are incubated with the recombinant 11cb splice variant, washed and cDNA clones which interact with 11cb splice variant isolated. Such methods are routinely used by skilled artisans. See, e.g., Sambrook (supra).

Another method is the screening of a mammalian expression library in which the cDNAs are cloned into a vector between a mammalian promoter and polyadenylation site and transiently transfected in COS or 293 cells. Forty-eight hours later the binding protein is detected by incubation of fixed and washed cells with a labelled 11cb splice variant. In a preferred embodiment, the 11cb splice variant is iodinated, and detection of any bound 11cb splice variant is viaautoradiography. See Sims, et al.,. *Science*,(1988), 241: 585–589 and McMahan, et al., *EMBO J.*, (1991), 10: 2821–2832. In this manner, pools of cDNAs containing the cDNA encoding the binding protein of interest can be selected and the cDNA of interest can be isolated by further subdivision of each pool followed by cycles of transient transfection, binding and autoradiography. Alternatively, the cDNA of interest can be isolated by transfecting the entire cDNA library into mammalian cells and panning the cells on a dish containing the 11cb splice variant bound to the plate. Cells which attach after washing are lysed and the plasmid DNA isolated, amplified in bacteria, and the cycle of transfection and panning repeated until a single cDNA clone is obtained. See Seed, et al, *Proc. Natl. Acad. Sci. USA*, (1987), 84: 3365 and Aruffo, et al., *EMBO J.* (1987)6: 3313. If the binding protein is secreted, its cDNA can be obtained by a similar pooling strategy once a binding or neutralizing assay has been established for assaying supernatants from transiently transfected cells. General methods for screening supernatants are disclosed in Wong, et al., *Science*, (1985), 228: 810–815.

Another alternative method is isolation of proteins interacting with the 11cb splice variant directly from cells. Fusion proteins of 11cb splice variant with GST or small peptide tags are made and immobilized on beads. Biosynthetically labeled or unlabeled protein extracts from the cells of interest are prepared, incubated with the beads and washed with buffer. Proteins interacting with the 11cb splice variant are eluted specifically from the beads and analyzed by SDS-PAGE. Binding partner primary amino acid sequence data are obtained by microsequencing. Optionally, the cells can be treated with agents that induce a functional response such as tyrosine phosphorylation of cellular proteins. An example of such an agent would be a growth factor or cytokine such as interleukin-2.

Another alternative method is immunoaffinity purification. Recombinant 11cb splice variant is incubated with labeled or unlabeled cell extracts and immunoprecipitated with anti-11cb splice variant antibodies. The immunoprecipitate is recovered with protein A-Sepharose and analyzed by SDS-PAGE. Unlabelled proteins are labeled by biotinylation and detected on SDS gels with streptavidin. Binding partner proteins are analyzed by microsequencing. Further, standard biochemical purification steps known to those skilled in the art may be used prior to microsequencing.

Yet another alternative method is screening of peptide libraries for binding partners. Recombinant tagged or labeled 11cb splice variant is used to select peptides from a peptide or phosphopeptide library which interact with the 11cb splice variant. Sequencing of the peptides leads to identification of consensus peptide sequences which might be found in interacting proteins.

The 11cb splice variant binding partners identified by any of these methods or other methods which would be known to those of ordinary skill in the art, as well as those putative binding partners discussed above, can be used in the assay method of the invention. Assaying for the presence of the 11cb splice variant/binding partner complex are accomplished by, for example, the yeast two-hybrid system, ELISA or immunoassays using antibodies specific for the complex. In the presence of test substances which interrupt or inhibit formation of the 11cb splice variant/binding partner interaction, a decreased amount of complex will be determined relative to a control lacking the test substance.

Assays for free 11cb splice variant or binding partner are accomplished by, for example, ELISA or immunoassay using specific antibodies or by incubation of radiolabeled 11cb splice variant with cells or cell membranes followed by centrifugation or filter separation steps. In the presence of test substances which interrupt or inhibit formation of the 11cb splice variant/binding partner interaction, an increased amount of free 11cb splice variant or free binding partner is determined relative to a control lacking the test substance.

Polypeptides of the invention also can be used to assess 11cb splice variant binding capacity of 11cb splice variant binding molecules in cells or in cell-free preparations.

Agonists and Antagonists—Assays and Molecules

The 11cb splice variant of the present invention may be employed in a process for screening for compounds which activate (agonists) or inhibit activation (antagonists) of the receptor polypeptide of the present invention.

In general, such screening procedures involve providing appropriate cells which express the receptor polypeptide of the present invention on the surface thereof. Such cells include cells from mammals, yeast, Drosophila or *E. coli*. In particular, a polynucleotide encoding the receptor of the present invention is employed to transfect cells to thereby express the 11cb splice variant. The expressed receptor is then contacted with a test compound to observe binding, stimulation or inhibition of a functional response.

One such screening procedure involves the use of melanophores which are transfected to express the 11cb splice variant of the present invention. Such a screening technique is described in PCT WO 92/01810, published Feb. 6, 1992. Such an assay may be employed to screen for a compound which inhibits activation of the receptor polypeptide of the present invention by contacting the melanophore cells which encode the receptor with both the receptor ligand and a compound to be screened. Inhibition of the signal generated by the ligand indicates that a compound is a potential antagonist for the receptor, i.e., inhibits activation of the receptor.

The technique may also be employed for screening of compounds which activate the receptor by contacting such cells with compounds to be screened and determining whether such compound generates a signal, i.e., activates the receptor.

Other screening techniques include the use of cells which express the 11cb splice variant (for example, transfected CHO cells) in a system which measures extracellular pH changes caused by receptor activation. In this technique, compounds may be contacted with cells expressing the receptor polypeptide of the present invention. A second messenger response, e.g., signal transduction or pH changes, is then measured to determine whether the potential compound activates or inhibits the receptor.

Another such screening technique involves introducing RNA encoding the 11cb splice variant into Xenopus oocytes to transiently express the receptor. The receptor oocytes are then contacted with the receptor ligand and a compound to be screened. Inhibition or activation of the receptor is then determined by detection of a signal, such as, calcium, proton, or other ions, in the case of screening for compounds which are thought to inhibit activation of the receptor.

Another screening technique involves expressing the 11cb splice variant in which the receptor is linked to phospholipase C or D. Representative examples of such cells include, but are not limited to, endothelial cells, smooth muscle cells, and embryonic kidney cells. The screening may be accomplished as hereinabove described by detecting activation of the receptor or inhibition of activation of the receptor from the phospholipase second signal.

Another method involves screening for compounds which are antgonists, and thus inhibit activation of the receptor polypeptide of the present invention by determining inhibition of binding of labeled ligand to cells which have the receptor on the surface thereof. Such a method involves transfecting a eukaryotic cell with DNA encoding the 11cb splice variant such that the cell expresses the receptor on its surface. The cell is then contacted with a compound in the presence of a labeled form of a known ligand. The ligand can be labeled, e.g., by radioactivity. The amount of labeled ligand bound to the receptors is measured, e.g., by measuring radioactivity associated with transfected cells or membrane from these cells. If the compound binds to the receptor, the binding of labeled ligand to the receptor is inhibited as determined by a reduction of labeled ligand which binds to the receptors.

Another method involves screening for 11cb splice variant inhibitors by determining inhibition or stimulation of 11cb splice variant-mediated cAMP and/or adenylate cyclase accumulation. Such a method involves transfecting a eukaryotic cell with 11cb splice variant receptor to express the receptor on the cell surface. The cell is then exposed to potential antagonists in the presence of 11cb splice variant. The amount of cAMP accumulation is then measured. If the potential antagonist binds the receptor, and thus inhibits 11cb splice variant binding, the levels of 11cb splice variant-mediated cAMP, or adenylate cyclase, activity will be reduced or increased.

The present invention also provides a method for determining whether a ligand not known to be capable of binding to an 11cb splice variant receptor can bind to such receptor which comprises contacting a mammalian cell which expresses an 11cb splice variant receptor with the ligand under conditions permitting binding of ligands to the 11cb splice variant receptor, and detecting the presence of a ligand which binds to the receptor thereby determining whether the ligand binds to the 11cb splice variant receptor. The systems hereinabove described for determining agonists and/or antagonists may also be employed for determining ligands which bind to the receptor.

Examples of potential 11cb splice variant receptor antagonists include antibodies or, in some cases, oligonucleotides, which bind to the receptor but do not elicit a second messenger response such that the activity of the receptor is prevented.

Potential antagonists also include proteins which are closely related to the ligand of the 11cb splice variant receptor, i.e. a fragment of the ligand, which have lost biological function and when binding to the 11cb splice variant receptor, elicit no response.

A potential antagonist also includes an antisense construct prepared through the use of antisense technology. Antisense technology can be used to control gene expression through triple-helix formation or antisense DNA or RNA, both methods of which are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix -see Lee, et al. *Nucl. Acids Res.,* 6: 3073 (1979); Cooney, et al, *Science,* 241: 456 (1988); and Dervan, et al., *Science,* 251: 1360 (1991)), thereby preventing transcription and production of the 11cb splice variant receptor. The antisense RNA oligonucleotide hybridizes to the mRNA in vivo and blocks translation of the mRNA molecule to the 11cb splice variant receptor (antisense—Okano, J., *Neurochem.,* 56: 560 (1991); OLIGODEOXY-NUCLEOTIDES AS ANTISENSE INHIBITORS OF GENE EXPRESSION, CRC Press, Boca Raton, Fla. (1988)). The oligonucleotides described above can also be delivered to cells such that the antisense RNA or DNA may be expressed in vivo to inhibit production of the 11cb splice variant receptor.

Another potential antagonist is a small molecule which binds to the 11cb splice variant receptor, making it inaccessible to ligands such that normal biological activity is prevented. Examples of small molecules include, but are not limited to, small peptides or peptide-like molecules.

Potential antagonists also include soluble forms of 11cb splice variant receptor, e.g., fragments of the receptor, which bind to the ligand and prevent the ligand from interacting with membrane bound 11cb splice variant receptors.

The 11cb splice variant proteins are ubiquitous in the mammalian host and are responsible for many biological functions, including many pathologies. Accordingly, it is desirous to find compounds and drugs which stimulate the 11cb splice variant on the one hand and which inhibit the function of an 11cb splice variant on the other hand.

In general, agonists for an 11cb splice variant receptor are employed for therapeutic and prophylactic purposes for such diseases or disorders as infections, such as bacterial, fungal, protozoan and viral infections, particularly infection caused by HIV-1 or HIV-2; pain; cancers; diabetes; obesity; anorexia; bulimia; asthma; Parkinson's disease; both acute and congestive heart failure; hypotension; hypertension; urinary retention; osteoporosis; angina pectoris; myocardial infarction; ulcers; allergies; benign prostatic hypertrophy and psychotic and neurological disorders, including anxiety, schizophrenia, manic depression, delirium, dementia or severe mental retardation; or dyskinesias, such as Huntington's disease or Gilles dela Tourett's syndrome, among others.

Antagonists for the 11cb splice variant may be employed for a variety of therapeutic and prophylactic purposes for such diseases or disorders as infections, including bacterial, fungal, protozoan and viral infections, particularly infection caused by HIV-1 or HIV-2; pain; cancers; diabetes; obesity; anorexia; bulimia; asthma; Parkinson's disease; both acute and congestive heart failure; hypotension; hypertension; urinary retention; osteoporosis; angina pectoris; myocardial infarction; ulcers; allergies; benign prostatic hypertrophy and psychotic and neurological disorders, including anxiety, schizophrenia, manic depression, delirium, dementia or severe mental retardation; or dyskinesias, such as Huntington's disease or Gilles dela Tourett's syndrome, among others.

This invention additionally provides a method of treating an abnormal condition related to an excess of 11cb splice variant activity which comprises administering to a subject the inhibitor compounds (antagonists) as hereinabove described along with a pharmaceutically acceptable carrier in an amount effective to inhibit activation by blocking binding of ligands to the 11cb splice variant, or by inhibiting a second signal, and thereby alleviating the abnormal conditions.

The invention also provides a method of treating abnormal conditions related to an under-expression of 11cb splice variant activity which comprises administering to a subject a therapeutically effective amount of a compound which activates the receptor polypeptide of the present invention (agonists) as described above in combination with a pharmaceutically acceptable carrier, to thereby alleviate the abnormal conditions.

Compositions and Kits

The soluble form of the 11cb splice variant, and compounds which activate or inhibit such receptor, may be employed in combination with a suitable pharmaceutical carrier. Such compositions comprise a therapeutically effective amount of the polypeptide or compound, and a pharmaceutically acceptable carrier or excipient. Such a carrier includes but is not limited to, saline, buffered saline, dextrose, water, glycerol, ethanol, and combinations thereof. The formulation should suit the mode of administration.

The invention further relates to pharmaceutical packs and kits comprising one or more containers filled with one or more of the ingredients of the aforementioned compositions of the invention.

Administration

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. More recently, alternative means for systemic administration of the compositions have been devised, which include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the patient's condition, and the judgment of the attending physician. Suitable dose ranges, however, are in the range of 0.1–100 µg/kg of subject. Wide variations in the needed dosage, however, are to be expected in view of the variety of peptides available and the differing efficiencies of various routes of administration. For example, oral administration would be expected to require higher dosages than administration by intravenous injection. Variations in these dosage levels can be adjusted using standard empirical routines for optimization, as is well understood in the art.

Gene Therapy

The 11cb splice variant polynucleotides, polypeptides, agonists and antagonists that are polypeptides may be employed in accordance with the present invention by expression of such polypeptides in vivo, in treatment modalities often referred to as "gene therapy."

Thus, for example, cells from a patient may be engineered with a polynucleotide, such as a DNA or RNA, to encode a polypeptide ex vivo. The engineered cells can then be provided to a patient to be treated with the polypeptide. For example, cells may be engineered ex vivo by the use of a retroviral plasmid vector containing RNA encoding a polypeptide of the present invention. Such methods are well-known in the art and their use in the present invention will be apparent from the teachings herein.

Similarly, cells may be engineered in vivo for expression of a polypeptide in vivo by procedures known in the art. For example, a polynucleotide of the invention may be engineered for expression in a replication defective retroviral vector, as discussed above. The retroviral expression construct may then be isolated and introduced into a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention should be apparent to those skilled in the art from the teachings of the present invention.

Retroviruses from which the retroviral plasmid vectors herein above mentioned may be derived include, but are not limited to, Moloney Murine Leukemia Virus, Spleen Necrosis Virus, Rous Sarcoma Virus, Harvey Sarcoma Virus, Avian Leukosis Virus, Gibbon Ape Leukemia Virus, Human Immunodeficiency Virus, Adenovirus, Myeloproliferative Sarcoma Virus, and Mammary Tumor Virus. In a preferred embodiment, the retroviral plasmid vector is derived from Moloney Murine Leukemia Virus.

Such vectors well include one or more promoters for expressing the polypeptide. Suitable promoters which may be employed include, but are not limited to, the retroviral LTR; the SV40 promoter; and the human cytomegalovirus (CMV) promoter described in Miller, et al., *Biotechniques* 7: 980–990 (1989), or any other promoter (e.g., cellular promoters such as eukaryotic cellular promoters including, but not limited to, the histone, RNA polymerase III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention will be placed under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs herein above described); the β-actin promoter; and human growth hormone promoters. The promoter may also be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, Ψ-2, Ψ-AM, PA12, T19-14X, VT-19-17-H2, YCRE, YCRIP, GP+E-86, GP+envAm12, and DAN cell lines as described in Miller, A., HUMAN GENE THERAPY 1: 5–14 (1990). The vector may be transduced into the packaging cells through any means known in the art. Such means include, but are not limited to, electroporation, the use of liposomes, and CaPO4 precipitation. In one alternative, the retroviral plasmid vector may be encapsulated into a liposome, or coupled to a lipid, and then administered to a host.

The producer cell line will generate infectious retroviral vector particles, which include the nucleic acid sequencer(s) encoding the polypeptides. Such retroviral vector particles may then be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

EXAMPLES

Certain terms used herein are explained in the foregoing glossary.

All examples are carried out using standard techniques, which are well known and routine to those of skill in the art, except where otherwise described in detail. Routine molecular biology techniques of the following examples can be carried out as described in standard laboratory manuals, such as Sambrook All parts or amounts set out in the following examples are by weight, unless otherwise specified.

Unless otherwise stated size separation of fragments in the examples below is carried out using standard techniques of agarose and polyacrylamide gel electrophoresis ("PAGE") in Sambrook and numerous other references such as, for instance, by Goeddel, et al., *Nucleic Acids Res.* 8: 4057.

Unless described otherwise, ligations are accomplished using standard buffers, incubation temperatures and times, approximately equimolar amounts of the DNA fragments to be ligated and approximately 10 units of T4 DNA ligase ("ligase") per 0.5 μg of DNA.

Example 1

Cloning of the 5'-end of the Human 11cb Splice Variant

The 5' end of the human 11cb splice variant was amplified by using the following primers and conditions on DNA from Human Whole Brain, purified from Life Technology's plasmid libraries.

The outside primers used were:

5' Vector-specific primer: 5' GCT ATT TAG GTG ACA CTA TAG AAG GTA CG 3' (SEQ ID NO: 3); and 3' Gene-specific primer: 5' CGA GAG GTT GAT GAT GAA GAT GTC 3' (SEQ ID NO: 4).

The following was used in a 50 microliter reaction volume: 10X Taq polymerase buffer, 200 μM dNTP, 5% glycerol, 50 picomoles of each primer, 100 nanograms of plasmid DNA from Human Whole Brain, purified from Life Technology's plasmid libraries, 1:10 by volume mixture of Taq polymerase and Pfu polymerase.

The following PCR program was then used:

1 cycle at 94° C. for 5 minutes;

25 cycles at 94° C. for 1 minute;

25 cycles at 55° C. for 1 minute;

25 cycles at 72° C. for 2 minutes; and 1 cycle at 72° C. for 8.5 minutes.

The nested or inside primers used were:

5' Vector-specific primer: 5' GGT GAC ACT ATA GAA GGT ACG 3' (SEQ ID NO: 5) and

3' Gene-specific primer: 5' GCA GAT GGT GCC GAA CAC CGA AGG 3' (SEQ ID NO: 6).

The nested or inside reaction used the same procedure as the outside reaction, except 1 μL of plasmid DNA was substituted with 1 μL of the outside reaction. The DNA was then size-fractionated on a 1.2% agarose gel. The 2 major bands were subcloned, and the subcloned fragments were sequenced. One of the major bands was the 5' end of the original human 11cb clone, disclosed in WO 96/18651, published Jun. 20, 1996, and the other band resulted in the cloning of the novel splice variant form of the human 11cb clone.

Example 2

Identification of Ligands or Antagonists

The expressed receptor described above in Example 1 is then screened for ligands or antagonists as follows.

A. Ligand/Tissue Banks

The expressed receptor is utilized to screen compound banks, complex biological fluids, combinatorial organic and peptide libraries, etc. to identify activating ligands or antagonists. Similarly, the receptors is screened against tissue extracts of human, and other mammalian, species, such as porcine tissue. Specifically such tissue extracts include lung, liver, gut, heart, kidney, adrenals, ischemic brain, plasma, urine and placenta. Extraction techniques employed in the formation of these tissue banks are known in the art.

B. Functional Assays

1. Xenopus Oocyte Assay

A Xenopus oocyte system is used in the characterization of cell surface receptors because these cells accurately translate mRNA and are capable of carrying out a large number of post-translational modifications, including signal peptide cleavage, glycosylation, phosphorylation and subunit assembly. A functional assay is performed as follows:

In vitro capped RNA transcripts are prepared from linearized plasmid templates encoding the 11cb splice variant receptor cDNA with RNA polymerases using standard protocols. In vitro transcripts are suspended in water at a final concentration of 0.2 mg/ml. Ovarian lobes are removed from adult female toad; stage V defolliculated oocytes are obtained and RNA transcripts (10 ng/oocyte) are injected in a 50 nl bolus using a Drummond microinjection apparatus. Two electrode voltage clamp (Warner Instruments) are used to measure the currents from individual Xenopus oocytes. Recordings are made in Ca2+free Barth's medium at room temperature.

2. Microphysiometer Assay

Screening of these banks is accomplished using a microphysiometer (commercially available from, e.g., Molecular Devices, Ltd.). For example activation of secondary messenger systems results in the extrusion of small amounts of acid from a cell, formed largely as a result of increased metabolic activity required to fuel the intracellular signaling process. The pH changes in the media surrounding the cell are small and detectable by the microphysiometer. Thus activation of any receptor which is coupled to an energy utilizing intracellular signaling pathway (e.g., andy G-protein coupled receptor) may be detectable.

3. Calcium Assay

Receptors stably expressed in HEK 293 cells can demonstrate a robust calcium response to agonists with the appropriate rank order and potency. Basal calcium levels in the HEK 293 cells in receptor-transfected or vector control cells is in the normal 100 nM to 200 nM range. HEK 293 cells expressing recombinant receptors are loaded with fura 2 and in a single day >150 selected ligands are evaluated for agonist-induced calcium mobilization. Agonists presenting a transient calcium mobilization are tested in vector control cells to determine if the calcium response was unique to the transfected receptor cells. When a unique agonist-induced response is identified, the response is reproduced in a separate group of cells and then pharmacologically characterized with concentration response curves for the effective and related ligands.

Example 2

Northern Blot Analysis

The northern blots used were purchased from Clontech. The transcript size was approximately 2.4 kb, and a transcript band was observed in whole brain, amygdala, caudate nucleus, corpus callosum, hippocampus, substantia nigra, subthalamic nucleus, thalamus, heart, and liver. Conversely, no transcript bands were detected by northern blot analysis in the following tissues: placenta, lung, skeletal muscle, kidney, or pancreas.

All publications including, but not limited to, patents and patent applications, cited in this specification, are herein incorporated by reference as if each individual publication were specifically and individually indicated to be incorporated by reference herein as though fully set forth.

The above description fully discloses the invention, including preferred embodiments thereof Modifications and improvements of the embodiments specifically disclosed herein are within the scope of the following claims. Without further elaboration, it is believed that one skilled in the art can, using the preceding description, utilize the present invention to its fullest extent. Therefore, the examples provided herein are to be construed as merely illustrative and are not a limitation of the scope of the present invention in any way. The embodiments of the invention in which an exclusive property or privilege is claimed are defined as follows.

What is claimed is:

1. An isolated polynucleotide comprising a nucleotide sequence encoding a polypeptide having the amino acid sequence contained in SEQ ID NO:2.

2. The isolated polynucleotide of claim 1 wherein the polynucleotide is DNA.

3. The isolated polynucleotide of claim 1 wherein the polynucleotide is RNA.

4. The isolated polynucleotide of claim 1 wherein said nucleotide sequence comprises the entire length of the polynucleotide sequence contained in SEQ ID NO:1.

5. The isolated polynucleotide of claim 1 wherein said polynucleotide is RNA corresponding to the entire length of the nucleotide sequence contained in SEQ ID NO:1.

6. The isolated polynucleotide of claim 1 wherein said polynucleotide is RNA corresponding to the entire region of the polynucleotide contained in SEQ ID NO:1 encoding a polypeptide having the amino acid sequence contained in SEQ ID NO:2.

7. An isolated polynucleotide wherein said polynucleotide is fully complementary to the nucleotide sequence that encodes the polypeptide contained in SEQ ID NO:2.

8. The isolated polynucleotide of claim 7 wherein said polynucleotide is fully complementary to the polynucleotide sequence set forth in SEQ ID NO:1.

9. An expression vector comprising an isolated DNA or RNA molecule encoding a polypeptide comprising an amino acid sequence contained in SEQ ID NO:2 when said expression vector is present in a compatible host cell.

10. An isolated host cell transformed with the expression vector of claim 9.

11. A process for producing a polypeptide having the amino acid sequence contained in SEQ ID NO:2 comprising culturing the host cell of claim 10 in a medium under conditions sufficient for the expression of said polypeptide and recovering said polypeptide from the culture.

12. A process for producing a recombinant host cell comprising transforming or transfecting a cell with the expression vector of claim 9 such that the host cell, under appropriate culture conditions, expresses a polypeptide comprising the amino acid sequence contained in SEQ ID NO:2.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 1385 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
GGTGACACTA TAGAAGGTAC GCCTGCAGGT ACCGGTCCGG AATTCCCGGG TCGACCCACG      60

CGTCCGGGAG GGCAGTTGGG CTTGGAGGCG GCAGCGGCTG CCAGGCTACG GAGGAAGACC     120

CCCTTCCCGA CTGCGGGGCT TGCGCTCCGG GACAAGGTGG CAGGCGCTGG AGGCTGCCGC     180

AGCCTGCGTG GGTGGAGGGG AGCTCAGCTC GGTTGTGGGA GCAGGCGACC GGCACTGGCT     240

GGATGGACCT GGAAGCCTCG CTGCTGCCCA CTGGTCCCAA TGCCAGCAAC ACCTCTGATG     300

GCCCCGATAA CCTCACTTCG GCAGGATCAC CTCCTCGCAC GGGGAGCATC TCCTACATCA     360

ACATCATCAT GCCTTCGGTG TTCGGCACCA TCTGCCTCCT GGGCATCATC GGGAACTCCA     420

CGGTCATCTT CGCGGTCGTG AAGAAGTCCA AGCTGCACTG GTGCAACAAC GTCCCCGACA     480

TCTTCATCAT CAACCTCTCG GTAGTAGATC TCCTCTTTCT CCTGGGCATG CCCTTCATGA     540
```

```
TCCACCAGCT CATGGGCAAT GGGGTGTGGC ACTTTGGGGA GACCATGTGC ACCCTCATCA    600

CGGCCATGGA TGCCAATAGT CAGTTCACCA GCACCTACAT CCTGACCGCC ATGGCCATTG    660

ACCGCTACCT GGCCACTGTC CACCCCATCT CTTCCACGAA GTTCCGGAAG CCCTCTGTGG    720

CCACCCTGGT GATCTGCCTC CTGTGGGCCC TCTCCTTCAT CAGCATCACC CCTGTGTGGC    780

TGTATGCCAG ACTCATCCCC TTCCCAGGAG GTGCAGTGGG CTGCGGCATA CGCCTGCCCA    840

ACCCAGACAC TGACCTCTAC TGGTTCACCC TGTACCAGTT TTTCCTGGCC TTTGCCCTGC    900

CTTTTGTGGT CATCACAGCC GCATACGTGA GGATCCTGCA GCGCATGACG TCCTCAGTGG    960

CCCCCGCCTC CCAGCGCAGC ATCCGGCTGC GGACAAAGAG GGTGACCCGC ACAGCCATCG   1020

CCATCTGTCT GGTCTTCTTT GTGTGCTGGG CACCCTACTA TGTGCTACAG CTGACCCAGT   1080

TGTCCATCAG CCGCCCGACC CTCACCTTTG TCTACTTATA CAATGCGGCC ATCAGCTTGG   1140

GCTATGCCAA CAGCTGCCTC AACCCCTTTG TGTACATCGT GCTCTGTGAG ACGTTCCGCA   1200

AACGCTTGGT CCTGTCGGTG AAGCCTGCAG CCCAGGGGCA GCTTCGCGCT GTCAGCAACG   1260

CTCAGACGGC TGACGAGGAG AGGACAGAAA GCAAAGGCAC CTGATACTTC CCCTGCCACC   1320

CTGCACACCT CCAAGTCAGG GCACCACAAC ACGCCACCGG GAGAGATGCT CTCGTGCCGA   1380

ATTCC                                                               1385

(2) INFORMATION FOR SEQ ID NO:2:

(i) SEQUENCE CHARACTERISTICS:
        (A) LENGTH: 353 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Met Asp Leu Glu Ala Ser Leu Leu Pro Thr Gly Pro Asn Ala Ser Asn
 1               5                  10                  15

Thr Ser Asp Gly Pro Asp Asn Leu Thr Ser Ala Gly Ser Pro Pro Arg
                20                  25                  30

Thr Gly Ser Ile Ser Tyr Ile Asn Ile Ile Met Pro Ser Val Phe Gly
            35                  40                  45

Thr Ile Cys Leu Leu Gly Ile Ile Gly Asn Ser Thr Val Ile Phe Ala
        50                  55                  60

Val Val Lys Lys Ser Lys Leu His Trp Cys Asn Asn Val Pro Asp Ile
65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125

Thr Ser Thr Tyr Ile Leu Thr Ala Met Ala Ile Asp Arg Tyr Leu Ala
    130                 135                 140

Thr Val His Pro Ile Ser Ser Thr Lys Phe Arg Lys Pro Ser Val Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190
```

Gly Cys Gly Ile Arg Leu Pro Asn Pro Asp Thr Asp Leu Tyr Trp Phe
            195                 200                 205

Thr Leu Tyr Gln Phe Phe Leu Ala Phe Ala Leu Pro Phe Val Val Ile
210                 215                 220

Thr Ala Ala Tyr Val Arg Ile Leu Gln Arg Met Thr Ser Ser Val Ala
225                 230                 235                 240

Pro Ala Ser Gln Arg Ser Ile Arg Leu Arg Thr Lys Arg Val Thr Arg
            245                 250                 255

Thr Ala Ile Ala Ile Cys Leu Val Phe Phe Val Cys Trp Ala Pro Tyr
            260                 265                 270

Tyr Val Leu Gln Leu Thr Gln Leu Ser Ile Ser Arg Pro Thr Leu Thr
            275                 280                 285

Phe Val Tyr Leu Tyr Asn Ala Ala Ile Ser Leu Gly Tyr Ala Asn Ser
            290                 295                 300

Cys Leu Asn Pro Phe Val Tyr Ile Val Leu Cys Glu Thr Phe Arg Lys
305                 310                 315                 320

Arg Leu Val Leu Ser Val Lys Pro Ala Ala Gln Gly Gln Leu Arg Ala
            325                 330                 335

Val Ser Asn Ala Gln Thr Ala Asp Glu Glu Arg Thr Glu Ser Lys Gly
            340                 345                 350

Thr (2) INFORMATION FOR SEQ ID NO:3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

GCTATTTAGG TGACACTATA GAAGGTACG                                                 29

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

CGAGAGGTTG ATGATGAAGA TGTC                                                        24

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GGTGACACTA TAGAAGGTAC G                                                           21

(2) INFORMATION FOR SEQ ID NO:6:

-continued

```
    (i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GCAGATGGTG CCGAACACCG AAGG                                              24
```